(12) United States Patent
Solomonidou et al.

(10) Patent No.: US 7,985,427 B2
(45) Date of Patent: Jul. 26, 2011

(54) GASTRIC JUICE-RESISTANT DEVICE FOR RELEASING MUCOADHESIVE ACTIVE SUBSTANCE EXCIPIENTS, AND METHOD FOR PRODUCING THIS GASTRIC JUICE-RESISTANT DEVICE

(75) Inventors: Despina Solomonidou, Freiburg (DE); Markus Krumme, Neuwied (DE); Bodo Asmussen, Bendorf-Sayn (DE); Joerg Kreuter, Bad Homburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 961 days.

(21) Appl. No.: 10/475,785

(22) PCT Filed: Apr. 22, 2002

(86) PCT No.: PCT/EP02/04381
§ 371 (c)(1),
(2), (4) Date: Dec. 30, 2003

(87) PCT Pub. No.: WO02/085333
PCT Pub. Date: Oct. 31, 2002

(65) Prior Publication Data
US 2004/0137174 A1      Jul. 15, 2004

(30) Foreign Application Priority Data
Apr. 25, 2001 (DE) .................. 101 20 092

(51) Int. Cl.
*A61K 9/16* (2006.01)
*A61K 9/20* (2006.01)
*A61K 9/26* (2006.01)
*A61K 9/24* (2006.01)
*A61K 9/28* (2006.01)
*A61K 9/34* (2006.01)
*A61K 9/32* (2006.01)
*A61F 13/00* (2006.01)

(52) U.S. Cl. ........ 424/497; 424/496; 424/434; 424/464; 424/469; 424/472; 424/474; 424/481; 424/482

(58) Field of Classification Search ................ 424/489, 424/490, 497, 43, 44, 600, 717, 496, 434, 424/464, 469, 472, 474, 481, 482; 514/951, 514/964, 965
See application file for complete search history.

(56) References Cited

U.S. PATENT DOCUMENTS
4,138,013 A * 2/1979 Okajima .................. 206/528
(Continued)

FOREIGN PATENT DOCUMENTS
EP      0 516 141 A      12/1992
(Continued)

OTHER PUBLICATIONS

Basf Technical Information, http://www.basf.cl/quimicafina/nutricionhumana/infogeneral/vitaminas/hidrosolubles/Vitamina_b2.pdf, obtained on Feb. 2, 2009.*

(Continued)

*Primary Examiner* — Paddy Padmanabhan
*Assistant Examiner* — Abigail Fisher
(74) *Attorney, Agent, or Firm* — Birch, Stewart, Kolasch & Birch, LLP

(57) ABSTRACT

The invention relates to a gastric juice-resistant device for releasing active substance excipients having delayed intestinal passage from a gastric juice-resistant enclosure, and which serves to increase the active substance concentration in the intestines. The inventive device is characterized in that the active substance excipient containing at least one active substance is provided in the form of a multiparticulate preparation whose individual particles have mucoadhesive properties. The invention also relates to a method for producing said device.

40 Claims, 1 Drawing Sheet

U.S. PATENT DOCUMENTS

| | | | | |
|---|---|---|---|---|
| 4,289,751 A | * | 9/1981 | Windheuser | 424/466 |
| 4,455,305 A | * | 6/1984 | Rokos | 514/150 |
| 4,522,625 A | * | 6/1985 | Edgren | 424/473 |
| 4,851,231 A | * | 7/1989 | Urquhart et al. | 424/469 |
| 5,232,708 A | * | 8/1993 | Castillo et al. | 424/497 |
| 5,780,057 A | * | 7/1998 | Conte et al. | 424/468 |
| 6,156,771 A | * | 12/2000 | Rubin et al. | 514/330 |
| 2004/0137174 A1 | * | 7/2004 | Solomonidou et al. | 428/34.1 |

FOREIGN PATENT DOCUMENTS

| | | |
|---|---|---|
| WO | WO 98 24412 A | 6/1998 |
| WO | WO 00 32172 A | 6/2000 |
| WO | WO 00 41740 A | 7/2000 |
| WO | WO 00 66089 A | 11/2000 |

OTHER PUBLICATIONS

Dictionary.com, Definition of Enclose, obtained online at http://dictionary.reference.com/browse/enclose, downloaded on Dec. 2, 2009.*

Junginger et al., Deutsche Apotheker Zeitung, vol. 130, No. 15, pp. 791-801 (1990).

Lehr et al., Journal of Controlled Release, vol. 13, No. 1, (1990).

* cited by examiner

GASTRIC JUICE-RESISTANT DEVICE FOR RELEASING MUCOADHESIVE ACTIVE SUBSTANCE EXCIPIENTS, AND METHOD FOR PRODUCING THIS GASTRIC JUICE-RESISTANT DEVICE

This application is the national phase under 35 U.S.C. §371 of PCT International Application No. PCT/EP02/04381 which has an International filing date of Apr. 22, 2002, which designated the United States of America.

The invention relates to a gastric juice-resistant device for releasing mucoadhesive active substance excipients and which serves to increase the concentration of active substances in the intestines, especially in the upper small intestine. Furthermore, a process for producing the inventive device is described.

The local treatment of the intestines, for example of the inflamed or infected intestinal mucosa has heretofore required the frequent administration of relatively large doses of active substance. With conventional medicament forms, the active substances only have a short local duration of action, or the active substances reach the site of action only after systemic absorption, via the blood supply. Frequent administration of high doses of active substance involves a high risk for the patient of becoming affected by unwanted side effects of the high-dosed active substance.

Apart from the above, active substances are known which are absorbed to an appreciable degree only in a very limited region of the upper small intestine. This is called an absorption window. An example of a substance that is absorbed only in an upper section of the small intestine is riboflavin. But also for captopril, furosemide and atenolol there is such an absorption window. Such medicinal agents have low bioavailability when administered with conventional medicament forms.

Conventional medicament forms are therefore poorly suited for administering such substances or for treating disorders of the upper small intestine since these forms of administration are already passing the absorption window, that is the site of action, when a large part of the active substance has not yet been released, or they pass the absorption window so quickly that only a small part of the active substance can be absorbed by the body.

It is the object of the present invention to provide a form of medicament which increases the active substance concentration at the site of action or absorption by prolonging the retention time of the active substance excipients in the small intestine, especially in the upper small intestine portion in order to thereby improve the bioavailability of the active substance or active substances, and which avoids the above-mentioned disadvantages.

This object is achieved by a gastric juice-resistant device according to claim 1, with the sub-claims relating to especially useful embodiments of the invention.

Accordingly, the inventive gastric juice-resistant device comprises at least one active substance in the form of a multiparticulate preparation, whose individual particles have mucoadhesive properties.

For the purposes of this invention, the term "multiparticulate preparation" comprises all multiparticulate medicament forms known in pharmaceutical technology. These are preparation forms wherein a plurality of individual particles defines one dosage unit of the active substance. Preparations of this kind may be, for example, pellets, microcapsules, microspheres, tablets, films, and the like.

The individual particles of the multiparticulate preparations are characterized by mucoadhesive properties. The mucoadhesive individual particles of the device serve as active substance excipients and are released in the lumen of the bowels. After hydration, the mucoadhesive individual particles adhere to the intestinal epithelium, and deliver the active substance in a controlled fashion.

Thus, it is possible by means of the inventive mucoadhesive individual particles to prolong the retention time of the active substance at the site of action or in the vicinity of the site of action, as compared to conventional medicament forms, so that very much smaller doses are required for achieving the same therapeutic effect. This entails a reduction in the patients' risk of becoming affected by the unwanted side effects of highly dosed active substances.

In a preferred embodiment, the individual particles of the multiparticulate active substance preparation consist of a film of at least two layers. This at least two-layered film consists of at least one water-soluble, mucoadhesive matrix layer and a hydrophobic, insoluble and active substance impermeable backing layer. The mucoadhesive layer is characterized by its good and long-lasting capability of adhering to the intestinal mucosa, its excellent tissue tolerance and its toxicological harmlessness. Furthermore, the matrix layer contains one or more active substances. The hydrophobic backing layer prevents the quick dissolution of the Mucoadhesive layers of the individual particles, and their agglutination to each other. The hydrophobic backing layer is likewise well tolerated by the tissue and toxicologically safe. In addition, because of the impermeability of the backing layer to the active substance, delivery of the active substance can only take place in the direction of the mucosa. In this way, the active substance reaches the site of action, respectively the site of absorption, in a controlled manner and is not released to the lumen of the intestine in an uncontrolled fashion. By using these at least double-layered films, the bioavailability of active substances for the treatment of the intestines, or of active substances having an absorption window, is optimized.

The size of the individual particles of the multiparticulate preparation preferably may be 8 mm in diameter; particle sizes of up to 6 mm in diameter are especially preferred.

Using such small, respectively small-area, individual particles has the advantage of the intestinal peristalsis having only little influence on the adhesion of the individual particles to the mucosa. This ensures a long-lasting and narrow contact between the intestinal epithelium and the individual particles, so that a safe active substance transfer from the individual particle to the site of action, respectively of absorption, is ensured.

By contrast to large-area systems, the inventive small, respectively small-area, individual particles, having a diameter of not more than 8 mm, can in addition not lead to extensive irritations and inflammations of the mucosa. Compared to conventional medicament forms, the tolerance of the inventive device is thus considerably improved.

With preference, the device according to the invention is provided with a gastric juice-resistant enclosure consisting of a polymer material and surrounding the active substance excipients in a space-saving fashion. This polymer enclosure consists of a material which is resistant in the acidic gastric environment, but quickly decomposes in the intestinal juice, thereby releasing the mucoadhesive active substance excipients completely into the lumen of the bowels. To this end it is indispensable for the functioning of the polymer enclosure that it be insoluble and impermeable in the gastric juice at body temperatures, i.e. at temperatures of up to about 40° C. Suitable polymer materials for use as the gastric juice-resistant enclosure are, for instance, methacrylic acid/ethyl acrylate copolymers, hydroxypropyl methylcellulose phthalate, cellulose acetate phthalate or methacrylic acid ester.

With such a polymer enclosure it is possible to also apply such active substances as have a comparatively low stability in the acidic environment of the stomach, or which are subject to decomposition on account of the influence of enzymes occurring in the gastric environment, but which on the other hand are particularly well absorbed by the intestinal mucosa. Examples for such substances are proteins, peptides or hormones, such as insulin or octreotid, for example.

To set the necessary mechanical and physicochemical properties of the enclosure, such as strength, flexibility, sealing capacity, hydrophilicity, etc, the enclosure may, apart from the polymer material, contain a further modified polymer or further commonly used auxiliary substances. Examples of auxiliary substances that may possibly be required are plasticizers, wetting agents, matting agents, colorants, stabilizers and taste corrigents.

A further inventive variant of the polymer enclosure possesses a multi-layered structure. Such a structure may be on account of the fact that for reasons of manufacturing technology it may be of advantage or even necessary to assemble the polymer enclosure from several layers.

For the inventive device to be easier and more conveniently swallowed by the patients, it is useful for the polymer enclosure to be shaped so as to enable easy and safe peroral application. To this end, preference is given according to the invention to the administration form of a capsule, the manufacture of which takes place in accordance with standardized methods and which capsule is for the most part very well accepted by the patients.

In a particularly preferred embodiment, the device contains a blowing agent causing the dispersion of the multiparticulate active substance-containing preparation. In addition, the blowing agent accelerates the disintegration of the polymer enclosure and assists in releasing the individual particles. The expanding agent is activated by access of liquid.

Preferably the said blowing agent is a component producing gas on contact with body fluids (e.g. intestinal juice). The expansion mechanism of the expandable component of the device is the formation of gas upon contact with the intestinal juice.

The individual active substance excipients receive an impulse to emerge from the polymer enclosure by the gas being formed, so that they emerge from the polymer enclosure quickly and completely. This at the same time reduces the risk of the active substance-containing preparations becoming agglutinated with one another by contacting one another.

Although from a physiological point of view various gases are suitable, including e.g. nitrogen, the formation of carbon dioxide is particularly preferred since this gas can be easily obtained from harmless blowing agents. Suitable substances from which carbon dioxide can be released are various carbonates, such as sodium carbonate, potassium carbonate or ammonium carbonate, as well as corresponding hydrogen carbonates. For the sake of tolerance and of a high yield, however, a hydrogen carbonate, e.g. sodium hydrogencarbonate, is preferred according to the invention.

In addition, with respect to the composition of the blowing agent it is necessary to take into account the physiological conditions in the upper small intestine. The pH value in the duodenum is, in empty condition, between 5.5 and 6.5, whereas in the postprandial phase a drop to below pH 5.4 is observed. In the jejunum, pH values between 6.3 and 7.3 are measured. For these reasons, it is necessary to add an acid component to the blowing agent which upon access of water brings about the generation of gas. As acid components it is possible to use, for example, citric acid, tartaric acid or sodium hydrogenphosphate.

The inventive blowing agent, too, can be present as a multiparticulate preparation. It may be necessary to quickly bring a part of the blowing agent to action, for instance in order to accelerate the disintegration of the polymer enclosure. In addition, the blowing agent may be present as a powder mixture or as a preparation formed by using usual pharmaceutical auxiliaries, e.g. pressed pieces or pellets. Furthermore, it is possible for the purposes of the invention to incorporate the blowing agent in the multiparticulate active substance-containing preparation. However, it is particularly advantageous if the active substances and the expanding agents are spatially separated in the preparation, because this reduces the risk of incompatibilities.

For a correct release of the individual particles from the inventive device, the spatial arrangement of the active substance-containing as well as of the blowing agent-containing preparations is of great importance since the active substance excipients are to be ejected from the capsule with their mucoadhesive layer in front. Preference is given to an alternating arrangement of the active substance-containing and blowing agent-containing preparations within the device, so that the individual active substance-containing preparations are released from the device successively and with their mucoadhesive layer first. This embodiment also prevents the individual active substance-containing preparations from sticking to each other with their active substance-containing layers after being released.

The inventive device offers the possibility of controlling the release rate of the active substance or active substances by way of the type and the composition of the multiparticulate preparation (active substance excipient), independently of the properties of the polymer enclosure.

Thus, it is possible to optimize the polymer enclosure with respect to other important aspects such as strength, flexibility, sealing capacity or resistance to gastric juice, and it does not need to be adjusted to the control of the release rate.

The fact that there is a possibility of controlling the release rate largely independently of the polymer enclosure is of significance especially since there is a demand, according to which one and the same enclosure should absorb water, respectively enable the diffusion of water, not until coming into contact with the intestinal juice, and on the other hand be insoluble and impermeable in the gastric juice.

Devices according to the present invention can be therapeutically utilized for various purposes. Important application areas are the application of active substances for local treatment of the intestines, especially of the upper small intestine portion, in cases of infections of the intestinal mucosa, as well as in cases of inflammatory and chronically inflammatory intestinal affections, such as colitis ulcerosa or enteritis regionalis. Here, the inventive device leads to an improvement of the bioavailability of active substances having a so-called absorption window in the upper small intestine portion. It is moreover predestined for the application of active substances which are unstable in the gastric environment and which are absorbed well in the upper small intestine portion.

BRIEF DESCRIPTION OF THE DRAWINGS

The Figures illustrate a particularly suitable embodiment of the device according to the invention.

Figure 1:
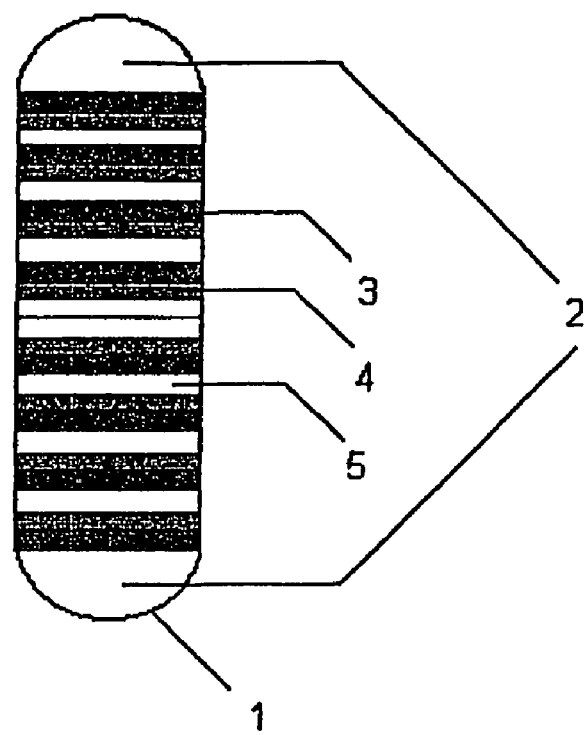
FIG. 1 shows a schematic section through an inventive device.
Figure 2:
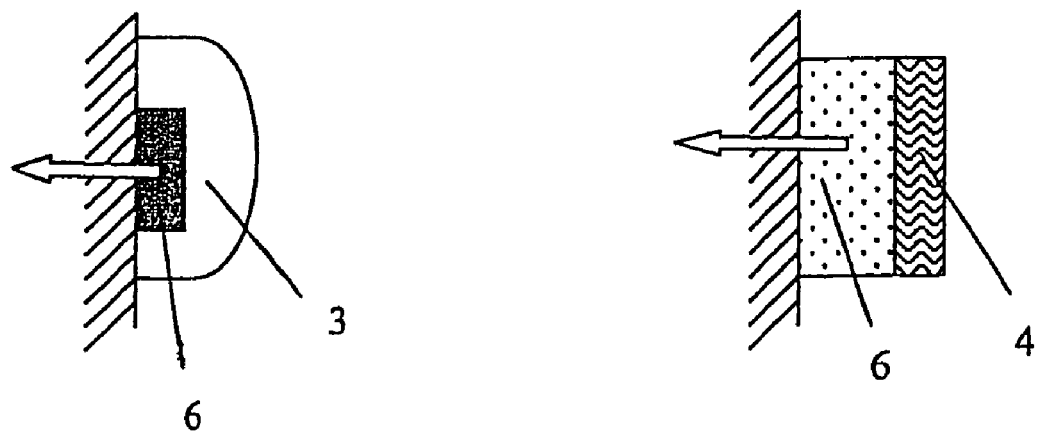
FIG. 2 shows two different embodiments of the active substance-containing individual particles in the state of releasing active substances.

In a preferred embodiment, illustrated by way of example in FIG. 1, there is provided a supply of gas-developing components (2 and 5) as well as a number of film-like, stacked individual particles which consist of a mucoadhesive, active substance-containing layer (3) and of a backing layer (4) controlling the direction of active substance release, these components being located within a polymer enclosure (1) which is resistant to gastric juice but permeable to intestinal juice. Here, the active substance (6) can be present embedded in the film-like component, as shown in FIG. 2.

The device according to the invention can be manufactured using a method with the following successive steps:
  a. transfer of a polymer material in web form to a moulding board provided with bores, and applying a vacuum to form the compartments of the polymer enclosure;
  b. alternately filling-in the active substance-containing preparation and the blowing agent-containing preparation;
  c. superposing a second polymer web, and closing the compartments by sealing with application of heat and pressure; and
  d. separating the individual devices by punching or cutting.

In the following, the inventive gastric juice-resistant device for releasing active substances having a delayed intestinal passage will be described by way of examples of embodiments for the manufacture with mucoadhesive active substance preparations. The following examples are not to be understood as limiting the present invention.

1. Preparation and Characterization of Double-layered Mucoadhesive Active Substance Excipients Substances serving as matrix-forming polymers of the mucoadhesive layer of the films were polyvinyl pyrrolidone (PVP), respectively polyvinyl alcohol (PVA). CARBOPOL® 934P (polymers of acrylic acid, cross-linked with allyl ethers of sucrose), CARBOPOL® 974NF (polymers of acrylic acid, cross-linked with allyl ethers of pentaerythritol) and polycarbophil (NOVEON™ AA1 (a high molecular weight acrylic acid polymer cross-linked with divinyl glycol)), as well as sodium carboxymethylcellulose (CMC) served as mucoadhesive polymers. Polyethylene glycol (PEG 600) was used as plasticizer. The concentration of the mucoadhesive polymer was varied between 0 and 20%-wt. To prepare the lipophile, non-mucoadhesive layer, cellulose acetate butyrate (CAB) was used as film former, titanium dioxide was used as pigment and diethyl phthalate was used as softener.

The polymer was initially strewn onto the solvent while stirring vigorously. Distilled water was used as solvent for polyvinyl alcohol, polyvinyl pyrrolidone and sodium carboxymethylcellulose; for cellulose acetate butyrate a mixture of ethyl acetate and absolute alcohol was used. In the case of the CAB solution, after adding the polymer, the pigment and the plasticizer were also added, and stirring was continued until a homogenous distribution and dissolution was achieved. To achieve complete dissolution of the polymers, stirring was continued for about 3 to 4 h at room temperature. In the case of PVA and PVP, the solutions were heated during this period in a water bath.

To prepare the polyacrylic acid suspensions, the polymer powders (1%-wt.) were dispersed in distilled water and subsequently the pH value of the dispersion was adjusted, while stirring strongly, with 1 N NaOH solution to 4.8, 5.5, 6.8 and 7.5.

Active substance-containing polymer preparations were prepared by adding riboflavin to the aqueous polyvinyl pyrrolidone solution, respectively polyvinyl alcohol solution, and by stirring under absence of light, up to dissolution of the active substance.

The coating mass for making the film was prepared from corresponding amounts of solutions of the mucoadhesive polymers, of the film-forming agents and of the plasticizers by mixing in a laboratory reactor with built-in stirrer until homogeneity was achieved.

The mucoadhesive films were made by coating on a carrier film. To this end the carrier film (HOSTAPHAN® RN 100 (biaxially oriented film made of polyethylene terephthalate (PET)) was placed on a horizontally oriented glass plate, and the mass for the mucoadhesive layer was applied by means of a doctor knife at a constant speed. The active substance-containing films were dried in the drying cupboard at 60° C. for 25 min, the riboflavin-containing films were dried overnight at the air, under absence of light. The dried films were subsequently coated in the same fashion with the mass for the lipophile layer. After drying in the drying cupboard for 15 min at 60° C., the films were punched out of the laminate in the desired shape using a punch with a handle.

Characterization of the active substance excipients was performed with regard to examining the adhesive power and the duration of adhesion on duodenal mucosa, to determining the water absorption capacity of the mucoadhesive layer, and also with regard to examining active substance release and active substance permeation. The examinations showed that formulations based on PVP had considerably better mucoadhesive properties than those with PVA as film matrix. In addition, it could be shown that there is a correlation between the concentration of the mucoadhesive polymer and the mucoadhesive properties of the formulation (adhesive power and duration of adhesion): the concentration in general has a positive influence on the adhesion potential. The degree of neutralisation of the polyacrylic acid derivative does also have an effect on the mucoadhesive properties of the film-like formulations, the optimum being at pH 5.5 and 6.8 of the aqueous polyacrylic acid dispersion. It was further-more proved that the release of the active substance takes place quickly and completely.

2. Preparation of Blowing Agent-containing Tablets

To prepare blowing agent-containing tablets, maize starch was used as filler, polyethylene glycol (PEG 400) was used as lubricant and a mixture of sodium hydrogencarbonate, crystalline tartaric acid and sodium dihydrogenphosphate was used as the blowing agent mixture.

Biplanar tablets of 8 mm in diameter were made by direct tableting using an instrumented excenter tableting press. The powdery auxiliaries (binding agent, lubricant and acid component) were mixed for 8 minutes in a tumbler. Subsequently, sodium hydrogencarbonate was added and this was again mixed. The tablets were stored in the desiccator over blue gel.

3. Preparation and Testing of Gastric Juice-resistant Capsules

To prepare the gastric juice-resistant capsules as primary medicament form for application of the mucoadhesive films, the aqueous dispersion of a copolymer of methacrylic acid and ethyl acrylate (Kollicoat® MAE) was used. To increase the viscosity, sodium carboxymethyl cellulose (CMC) was used. Diethyl phthalate was used as plasticizer. Gastric juice-resistant capsules were made from Kollicoat®MAE, CMC and diethyl phthalate in a ratio of 60:10:30 (mass content). The aqueous CMC solution is provided, and the 30%-wt. of Kollicoat® MAE dispersion as well as the plasticizer are added while stirring. The homogenous dispersion is applied to a carrier film with the aid of a doctor knife at constant speed. The films were subsequently dried in the drying cupboard at 60° C. for 30 minutes.

The films were transferred to the filling apparatus. This apparatus is a moulding board of metal with capsule-shaped, oval bores. By applying a vacuum in the individual bores, troughs were formed in the film, which were then alternately filled with the blowing agent-containing tablets and the double-layered, active substance-containing films. At both ends of the capsule there is in addition a blowing agent mixture. Subsequently a second film was placed thereon, with which the capsules were closed, by heating and pressing a fitting cover plate thereon, and punched out.

This special arrangement on the one hand serves to quickly release and on the other hand to disperse the films upon disintegration of the capsule wall. By the access of liquid, the blowing agent set of the tablets and of the powder mix is activated. The individual films receive an impulse to emerge from the capsule by the $CO_2$ being generated. The disintegration of the capsule starts at both ends, whereas the capsule shell initially remains intact. The films are ejected from the capsule with the mucoadhesive layer in front. This at the same time reduces the risk of the films becoming agglutinated by contact with each other. An advantage of this application form consists in the disintegration of the capsule not being a limiting factor to the active substance release: the capsule is capable of rapidly, individually and completely releasing the films. This was established by ex-vivo attempts with pig's intestine. In addition, the capsules were tested (by analogy to the European Pharmacopoeia) in a decomposition apparatus, initially in 0.1 N HCl at 37° C. for 2 h. During this process, none of the capsules showed any signs of disintegration or water permeability. Subsequently, the test was performed with phosphate buffer solution, pH 6.8, for 60 minutes. The capsules disintegrated within a short period of time and thus complied with the requirements of the pharmacopoeia.

The invention claimed is:

1. A gastric juice-resistant device for releasing active substance carriers which have a delayed intestinal passage from a gastric juice-resistant enclosure which disintegrates in the presence of intestinal juice, wherein
   the active substance carriers containing at least one active substance are present in the form of a multiparticulate preparation which is enclosed in said gastric juice-resistant enclosure,
   the individual particles of said multiparticulate preparation comprise a film of at least two layers, of which at least one has mucoadhesive properties and contains said active substance,
   the said device contains a blowing agent preparation comprising a blowing agent which generates gas on contact with liquid, said blowing agent causing the dispersion of the individual particles of the multiparticulate active substance-containing preparation,
   said blowing agent preparation is present as a powder mixture or as pressed pieces or as pellets or tablets,
   the said multiparticulate preparation and said blowing agent preparation are stacked on top of each other in an alternating fashion in said device, and
   said device having an elongated shape and two ends at opposite sides of the device, and said disintegration starts at said ends of the device.

2. The device according to claim 1, wherein the size of the individual particles of the multiparticulate preparation is up to 8 mm in diameter.

3. The device according to claim 1, wherein the individual particles of the multiparticulate preparation contain the active substance embedded in at least a part thereof.

4. The device according to claim 1, wherein the gastric juice-resistant enclosure consists of a polymer material.

5. The device according to claim 4, wherein the polymer enclosure has a single-layered or double-layered structure.

6. The device according to claim 4, wherein the polymer enclosure consists of a polymer material selected from the group consisting of copolymers of methacrylic acid and ethyl acrylate, hydroxypropyl methylcellulose phthalate, cellulose acetate phthalate and methacrylic acid ester.

7. The device according to claim 4, wherein the polymer enclosure is shaped such that a peroral application is made possible.

8. The device according to claim 1, wherein the blowing agent contains hydrogen carbonate, and/or generates carbon dioxide on contact with intestinal juice.

9. The device according to claim 1, wherein the blowing agent additionally contains an acid component.

10. The device according to claim 1, wherein the device contains at least one active substance selected from the group consisting of riboflavin, captopril, furosemide and atenolol.

11. The device according to claim 1, wherein the device contains at least one active substance which is selected from the group consisting of proteins, peptides and hormones.

12. The device according to claim 1, wherein the device contains at least one active substance which is selected from the group consisting of insulin and octreotid.

13. A process for the production of a gastric juice-resistant device, which device comprises at least one active substance in the form of a multiparticulate preparation whose individual particles have mucoadhesive properties, and a blowing agent preparation which on contact with liquid produces a gas, said individual particles being enclosed by a gastric juice-resistant, intestinal juice-soluble polymer enclosure, said process comprising the following steps:
   a. transfer of a polymer material in web form to a moulding board provided with bores, and applying a vacuum to form depressions in the web which serve as the compartments of the polymer enclosure;
   b. alternately filling-in the active substance-containing, multiparticulate preparation and the blowing agent-containing preparation into said compartments;
   c. superposing a second polymer web, and closing the compartments by sealing with application of heat and pressure; and
   d. separating the individual devices by punching or cutting.

14. The device according to claim 2, wherein the size of the individual particles of the multiparticulate preparation is up to 6 mm in diameter.

15. The device according to claim 1, wherein said film comprises a backing layer which is impermeable to the active substance.

16. The device according to claim 15, wherein said backing layer is hydrophobic and insoluble.

17. A gastric juice-resistant device for releasing active substance carriers which have a delayed intestinal passage from a gastric juice-resistant enclosure, wherein the active substance-containing carrier containing at least one active substance is present in the form of a multiparticulate preparation whose individual particles comprise a film of at least two layers, of which at least one has mucoadhesive properties and contains said active substance, and wherein said device further contains a blowing agent which generates gas on contact with liquid, said blowing agent being spatially separated from said active substance carriers, and said blowing agent and said active substance carriers being loosely arranged within said enclosure.

18. The device according to claim 17, wherein said film comprises a backing layer which is impermeable to the active substance.

19. The device according to claim 18, wherein said backing layer is hydrophobic and insoluble.

20. The device according to claim 1, wherein said device is orally administered.

21. The device according to claim 20, wherein the active substance carriers, upon oral administration, are released from the device into the lumen of the intestine and adhere to the intestinal epithelium.

22. The device according to claim 1, wherein said active substance-containing, mucoadhesive layer comprises one or more polymers selected from the group consisting of polyvinyl pyrrolidone, polyvinyl alcohol, polycarbophil, and sodium carboxymethyl cellulose.

23. The device according to claim 22, wherein said active substance-containing, mucoadhesive layer further comprises polyethylene glycol.

24. A method for treatment of a subject suffering from a riboflavin deficiency disorder, by application of riboflavin, said method comprising:
orally administering to said subject and thereafter swallowing of the gastric juice-resistant device as defined in claim 1 or claim 17,
wherein individual particles of said multiparticulate preparation have mucoadhesive properties and contain riboflavin, and
wherein the enclosure is soluble or decomposes in the intestinal juice or is permeable to intestinal juice.

25. A method for administering to a subject therapeutically active substances which are absorbed in the intestine and for increasing the concentration of said active substances in the intestine, said person being in need of said administration, which method comprises:
orally administering to said subject and thereafter swallowing of a gastric juice-resistant device as defined in claim 1 or claim 17.

26. The method according to claim 25, wherein said method is for administering therapeutically active substances selected from the group consisting of riboflavin, captopril, furosemide, atenolol, insulin and octreotide.

27. The device according to claim 17, wherein said blowing agent is present as a powder mixture or as pressed pieces or as pellets.

28. The device according to claim 17, wherein said blowing agent is contained in the said device as a further multiparticulate preparation.

29. The device according to claim 1, wherein said individual particles of said multiparticulate preparation are commonly enclosed by said gastric juice-resistant enclosure.

30. The device according to claim 1, wherein said individual particles of said multiparticulate preparation are releasably contained within said juice-resistant enclosure.

31. The device according to claim 1, wherein said juice-resistant enclosure is a capsule.

32. The device according to claim 1, wherein said gastric juice-resistant enclosure is a capsule having a lower end and an upper end, and said blowing agent preparation is additionally provided at both ends of the capsule.

33. A process for the production of a gastric juice-resistant device, which device comprises at least one active substance in the form of a multiparticulate preparation whose individual particles have mucoadhesive properties, and a blowing agent which on contact with liquid produces a gas, said individual particles being enclosed by a gastric juice-resistant, intestinal juice-soluble polymer enclosure, said process comprising the following steps:
a. transfer of a polymer material in web form to a moulding board provided with bores, and applying a vacuum to form depressions in the web which serve as the compartments of the polymer enclosure;
b. fillinq-in the blowing agent preparation into a lower end of said enclosure;
c. alternately filling-in the active substance-containing, multiparticulate preparation and the blowing agent-containing preparation into said compartments;
d. filling-in the blowing agent preparation into an upper end of said enclosure;
e. superposing a second polymer web, and closing the compartments by sealing with application of heat and pressure; and
f. separating the individual devices by punching or cutting.

34. The device according to claim 1, wherein the particles of said multiparticulate preparation further comprise a hydrophobic backing layer which is provided on the side opposite to the mucoadhesive layer, said backing layer being impermeable to the active substance.

35. The device according to claim 34, wherein the mucoadhesive layers of the stacked multiparticulate preparation are oriented in one direction relative to the stack, and the backing layers are oriented in the opposite direction.

36. The device according to claim 1, wherein said blowing agent is spatially separated from said active substance carriers, and said blowing agent and said active substance carriers being loosely arranged within said enclosure.

37. The device according to claim 1, wherein said blowing agent preparation does not contain said active substance.

38. The device according to claim 1, wherein said particles are pieces of films which are punched out of said film comprising at least two layers.

39. A gastric juice-resistant device for releasing active substance carriers which have a delayed intestinal passage from a gastric juice-resistant enclosure, wherein the active substance-containing carrier containing at least one active substance is present in the form of a multiparticulate preparation whose individual particles are pieces of film, which pieces are obtained from a film of at least two layers, of which at least one has mucoadhesive properties and contains said active substance, and wherein said device further contains a blowing agent which generates gas on contact with liquid, said blowing agent being spatially separated from said active substance carriers, and said blowing agent and said active substance carriers being loosely arranged within said enclosure.

40. The device according to claim 1, wherein the multiparticulate preparation and the blowing agent preparation constitute the filling of the enclosure.

* * * * *